US012635901B2

(12) United States Patent
Kawecki et al.

(10) Patent No.: US 12,635,901 B2
(45) Date of Patent: May 26, 2026

(54) METHOD AND APPARATUS FOR DETERMINING POTENTIAL ONSET OF AN ACUTE MEDICAL CONDITION

(71) Applicant: RESMED SENSOR TECHNOLOGIES LIMITED, Dublin (IE)

(72) Inventors: Katherine Kawecki, West Ryde (AU); Christian Reeks, West Ryde (AU)

(73) Assignee: ResMed Sensor Technologies Limited (IE)

( * ) Notice: Subject to any disclaimer, the term of this patent is extended or adjusted under 35 U.S.C. 154(b) by 1012 days.

(21) Appl. No.: 17/055,379

(22) PCT Filed: May 14, 2019

(86) PCT No.: PCT/AU2019/050455
§ 371 (c)(1),
(2) Date: Nov. 13, 2020

(87) PCT Pub. No.: WO2019/218008
PCT Pub. Date: Nov. 21, 2019

(65) Prior Publication Data
US 2021/0186368 A1 Jun. 24, 2021

(30) Foreign Application Priority Data

May 14, 2018 (AU) ................................ 2018901651

(51) Int. Cl.
*A61B 5/08* (2006.01)
*A61B 5/00* (2006.01)
(Continued)

(52) U.S. Cl.
CPC .............. *A61B 5/0803* (2013.01); *A61B 5/08* (2013.01); *A61B 5/1112* (2013.01); *A61B 5/4842* (2013.01); *A61B 5/6833* (2013.01); *A61B 5/725* (2013.01); *A61B 5/7264* (2013.01); *A61B 5/7267* (2013.01); *A61B 5/7275* (2013.01);
(Continued)

(58) Field of Classification Search
None
See application file for complete search history.

(56) References Cited

U.S. PATENT DOCUMENTS

| | | | | |
|---|---|---|---|---|
| 5,902,250 A | * | 5/1999 | Verrier | ................. A61B 5/4818 |
| | | | | 600/513 |
| 6,517,497 B2 | * | 2/2003 | Rymut | ................. A61B 5/6833 |
| | | | | 600/533 |

(Continued)

OTHER PUBLICATIONS

International Search Report and Written Opinion for PCT/AU2019/050455 dated Aug. 5, 2019.

*Primary Examiner* — Michael R Bloch
(74) *Attorney, Agent, or Firm* — Botos Churchill IP Law LLP

(57) ABSTRACT

Disclosed is a method of managing risk, of a subject, of suffering an adverse condition relating to a physiological system of the subject. The method includes a. providing a wearable acoustic sensor, b. providing a data processor, and c. causing the processor to i. monitor the output from the sensor, ii. apply a predictive numerical model to generate a prediction, iii. compare the prediction with the sensor output, and iv. determine a response on the basis of the comparison.

11 Claims, 3 Drawing Sheets

(51) Int. Cl.

| | |
|---|---|
| *A61B 5/11* | (2006.01) |
| *A61B 7/00* | (2006.01) |
| *A61B 7/04* | (2006.01) |
| *G08B 21/02* | (2006.01) |
| *G08B 21/04* | (2006.01) |
| *G08B 27/00* | (2006.01) |
| *G16H 10/60* | (2018.01) |
| *G16H 50/20* | (2018.01) |

(52) U.S. Cl.
CPC ............ *A61B 5/7282* (2013.01); *A61B 5/746* (2013.01); *A61B 5/747* (2013.01); *A61B 7/003* (2013.01); *A61B 7/04* (2013.01); *G08B 21/02* (2013.01); *G08B 21/0453* (2013.01); *G08B 27/006* (2013.01); *G16H 10/60* (2018.01); *G16H 50/20* (2018.01); *A61B 2560/0209* (2013.01); *A61B 2562/0204* (2013.01)

(56) References Cited

U.S. PATENT DOCUMENTS

| | | | |
|---|---|---|---|
| 9,131,902 B2 | 9/2015 | Halperin et al. | |
| 2005/0119586 A1 | 6/2005 | Coyle et al. | |
| 2008/0114260 A1 | 5/2008 | Lange et al. | |
| 2015/0164433 A1* | 6/2015 | Halperin .............. | A61B 5/0823 600/300 |
| 2015/0335288 A1* | 11/2015 | Toth .................... | A61B 5/6833 600/391 |

* cited by examiner

METHOD AND APPARATUS FOR DETERMINING POTENTIAL ONSET OF AN ACUTE MEDICAL CONDITION

CROSS REFERENCE TO RELATED APPLICATIONS

This application is a U.S. national stage application under 35 U.S.C. § 371 (b) of International Application No. PCT/AU2019/050455 filed May 14, 2019, which claims priority to Australian Patent Application No. 2018901651 filed on May 14, 2018, the disclosures of both of which are hereby expressly incorporated by reference in their entirety.

FIELD OF INVENTION

The present disclosure relates to an apparatus and method for managing risk, of a subject, of suffering an adverse condition. Such an apparatus and method may predict the potential onset of an acute medical condition. The method and apparatus may use feedback on functioning of a physiological function and means for detecting a change in that function that may constitute a prelude to an acute medical condition. The invention relates to, but is not limited to, respiratory conditions or to the specific prevention or alleviation of asthma symptoms.

BACKGROUND TO THE INVENTION

A significant operating cost borne by national economies relates to the cost of avoidable medical treatment and preventable conditions developing. Asthma is an ailment that affects growing numbers of patients for reasons not yet fully understood.

A person in the throes of an asthma attack—and especially whilst suffering mind-clouding asthma symptoms such as shortness of breath and panic—may experience confusion and uncertainty about which medication to use and when and how to administer it using their inhaler.

It is thought that early detection of changes in respiratory function may enable pre-emptive avoidance of life-threatening symptoms developing.

U.S. Pat. No. 8,807,131 discloses a device that can monitor a patient's compliance with an asthma inhaler treatment regimen. It has a motion sensor to monitor the motion of an asthma inhaler for typical use and a temperature sensor to indicate patient proximity and allow a deduction to be made that a patient is using the device. Alerts are issued via a smartphone relating to compliance with the treatment regimen. The device does not function to sense the onset of an acute attack of asthma.

US patent application publication no. 2011/0125044 describes an automated monitoring system for respiratory diseases, monitoring respiratory signs and symptoms indicating whether a patient is experiencing an acute event. Time domain and frequency domain analyses of signals are performed and spectral content of candidate sounds is employed to discriminate symptoms of interest from background sounds and to establish significance. They may be used in predicting future respiratory events.

An experimental device, described in patent application publication US20170071506A1, monitors current asthma symptoms and allows the user to view and draw their own conclusions about their current condition. Other devices based on symptom detection and/or monitoring of medication usage include Airsonea by Respiri, Inspiromatic by InspiroMedical, Smartinhaler by adherium, CareTRx Sensor and Propeller by Propeller Health.

In Australia, the only pre-emptive asthma treatment available is a personal asthma plan drawn up manually for a given patient by a general practitioner (GP) or respiratory specialist. It consists of daily preventer medication and reliever medication (typically sold under the trade mark Ventolin® typically), which the patient self-administers when they feel it is required.

Current asthma treatment is therefore very much focused on reaction to symptoms. Some records show that 84% of children hospitalised for asthma already owned a nebuliser, being a device that delivers large amounts of the medication, usually salbutamol, to force open airways. There are many examples of nebulisers available, for example the device available under the brand InnoSpire Deluxe by Philips Respironics.

The present inventors have discerned a need for a system that empowers a user to take control of a threatening medical situation and facilitates and promotes behavioural change in the long-term management of the condition giving rise to the situation. This is especially so in the case of asthma.

The preceding discussion of the background to the invention is intended to facilitate an understanding of the present invention. However, it should be appreciated that the discussion is not an acknowledgement or admission that any of the material referred to was part of the common general knowledge in Australia or elsewhere as of the priority date of the present application.

Further, and unless the context clearly requires otherwise, throughout the description and the claims, the words 'comprise', 'comprising', and the like are to be construed in an inclusive sense, meaning "including, but not being limited to"—as opposed to an exclusive or exhaustive sense, meaning "including this and nothing else".

SUMMARY OF INVENTION

Disclosed herein are anticipatory, preventative approaches that represent a paradigm shift in asthma treatment. In particular, disclosed is a device for use in a predictive method of managing a chronic medical condition, such as asthma. The method extends optionally to employing machine learning of patient response to physiological change and assessing a need for intervention based on analysis of stored data. This assessment may therefore be based on the specific response of the patient to physiological change and/or treatment. Recordings taken—e.g. by an acoustic sensor—, a prediction made for each recording, and/or a response determined for each recording may be stored in memory (e.g. a database). The prediction is, in effect, a determination of whether or not the patient will experience an acute medical condition such as an asthma attack. Similarly, the response may be the change in condition of the patient based on subsequent recordings or measurements. This will allow development or refinement of a machine learning model that applies known processes to categorise new recordings and predictions (e.g. whether or not they indicate impending onset of an acute medical condition or event), and determine responses, by reference to a progressively improved and growing data set.

The method may include the steps of collecting physiological condition (e.g. respiratory rate, period of respiration, heart rate) signals from one or more sensors, thereby to monitor a patient's health condition and alert the patient to an anticipated imminent medical issue of concern via audio, visual and/or tactile feedback. Sensors may include any one or more of audio/acoustic, electrocardiogram (ECG), electromyography (EMG), location (e.g. via a global positioning system (GPS)) and the like. The method may be sensor-agnostic. Where necessary, analog signals are converted to digital outputs and then deconstructed to principal components. The principal components are correlated via machine learning to identify specific health conditions and trends pertaining to the individual wearer are displayed. When a patient exhibits signals that correlate to a preliminary development that has been shown in that patient (e.g. in labelled historical data for the patient) to result in an acute attack occurring, an anticipatory alert is issued so that the patient or their carer may act pre-emptively to prevent or at least alleviate such an attack. If appropriate measures are taken to alleviate an attack, subsequent recordings may show the patient has recovered. This may incorrectly result in an accurate prediction that an acute condition is imminent, being classified as indicative of there being no impending danger. To avoid remedial treatment polluting the data set, measurements on which predictions were made and in response to which remedial action was taken may be disregarded or otherwise categorised so those measurements do not ultimately form part of the data set indicating that no acute medical condition is imminent.

Disclosed herein is a method of managing patient risk for a patient at risk of suffering an acute medical condition relating to a physiological system of said patient, the method comprising steps of:

a. providing the patient with a wearable acoustic sensor, operatively configured to provide output relating to sensed cyclical events in the functioning of said physiological system;

b. providing a data processor in data communication with the sensor and c. causing the processor to:

i. monitor output from the sensor relating to said observed cyclical events, ii. apply a predictive numerical model to generate, from output relating to an event in the most recently observed event cycle, a prediction of output from the sensor in relation to the corresponding event in a future cycle to be observed, iii. compare the prediction with the sensor output relating to the corresponding event in the future cycle when observed, and iv. determine a response on the basis of the comparison.

As used herein:

an "observation" made by a sensor is equivalent to something—e.g. a physiological parameter—the sensor has "sensed".

an "adverse condition" may be an "acute medical condition".

a "subject" may be a patient, or a patient or person at risk of suffering an acute medical condition, or may be a healthy subject.

Similarly, the phrase "relating to said observed cyclical events" may refer to a signal in which the cyclical event is represented, such as an acoustic signal from which inhalation and exhalation periods and features (e.g. rasping noise) can be determined. The wearable acoustic sensor may be on board a device that also includes the processor, for processing signals, and the acoustic sensor and signal process may be in data communication. The sensor, and thus the device incorporating it, may be "operatively configured" by being "operatively applied" to a selected portion of the subject's skin. Similarly, being "operatively applied" refers to being located on and/or attached to the skin of the patient such that the sensor, and device in general, can perform its function. For example, "operatively configured" may mean located to capture an acoustic signal—e.g. on the chest or neck of the wearer—indicative of respiratory function of the patient, or otherwise configured to capture an acoustic signal from which respiratory function can be determined. Steps c.i. to c.iv. may be performed by:

i. isolating and storing in memory a principal component, of the signal, corresponding to the respective breath;

ii. utilising at least one stored principal component in generating a prediction of a principal component of a future signal relating to the next expected breath of the patient;

iii. isolating from the patient's next breath an actual principal component thereof;

iv. determine the variance between actual and prediction; and v. if the variance exceeds a pre-set limit, output an alert of an imminent acute condition arising.

The predictive numerical model preferably comprises extended Kalman filtering (EKF), and in applying the numerical model the processor performs EKF on a component of the sensor output.

Further preferably, the method comprises performing principal component analysis on the sensor output to identify the component on which to perform the EKF.

Still more preferably, EKF is performed on the identified principal component only.

According to a preferred form of the invention, the future cycle is the next cycle after the most recently observed cycle. Similarly, the future signal may be the signal measured for the future cycle.

In a further preferred form of the invention, the sensor output relates to an acoustic signal detected in the functioning of said physiological system.

In a still further preferred form of the invention, the response comprises sending data used in the comparison to a machine learning model and causing the model to consult a database of historical output and predictions for determining whether the comparison indicates an acute condition is imminent. The historical data may comprise prior recordings for the particular patient and/or a pool of patients. The historical data may also comprise a prediction and/or a response determined according to the method above, for each recording.

The historical data may also comprise information relating to the predictability of the subject's breathing. Incorrect predictions may indicate that the subject's breathing is abnormal, or not in line with their previous predictions. For example, where a previous prediction indicating the impending onset of an acute medical condition, yet no such condition precipitated in relation to a more recent recording, the patient's breathing may have improved. Conversely, where a previous prediction did not indicate the impending onset of an acute medical condition, yet such a condition precipitated in relation to a more recent recording, the patient's breathing may be abnormal (e.g. due to pollen being in the air) and, in severe cases, may have deteriorated—i.e. respiratory function has decreased.

In a yet further preferred form of the invention, the method also includes allocating increased processing resources to running the machine learning model when the comparison yields a disparity between the prediction and the corresponding event in said future cycle.

In the event an acute condition is indicated, the method preferably includes causing the processor to output an alert signal for receiving by the subject (e.g. patient) and one or more of carer or medical practitioner of the patient.

In a preferred embodiment of the invention, the alert signal comprises haptics.

The method may further include subjecting the sensor output to preliminary filtering before performing principal component analysis.

In a preferred embodiment of the invention, the physiological function concerns respiratory function and the acute medical condition is asthma. Respiratory function may be determined many ways—e.g. inhalation/exhalation ratio, mucus build up, muscle constriction, expansion and contraction, chemical composition of exhaled breath, temperature of exhaled breath—indicating, e.g. inflammation in lungs—, respiratory rate, blood oxygen level, quiet and consistent breathing sounds and so forth. Similarly, sensors used to assess respiratory function will match the parameters being measured—e.g. audio sensors for measuring breathing sounds, chest belt for measuring chest expansion and contraction.

According to a second aspect of the invention, there is provided a wearable medical condition-management device wearable by a patient at risk of suffering an acute medical condition relating to a physiological system of said patient, the device comprising:

d. an acoustic sensor operatively configured to provide output relating to observed cyclical events in the functioning of said physiological system, and e. a computer processor in data communication with the sensor, the processor being programmed to execute instructions causing it to:

i. monitor output from the sensor relating to said observed cyclical events, ii. apply a predictive numerical model to generate, from output relating to an event in the most recently observed event cycle, a prediction of output from the sensor in relation to the corresponding event in a future cycle to be observed, iii. compare the prediction with the sensor output relating to the corresponding event in the future cycle when observed, and iv. determine a response on the basis of the comparison.

The wearable device may be a medical condition-anticipation device. The processor may be a microprocessor in data communication with the acoustic sensor to collect the signal therefrom. The signal may relate to respiratory function of the subject, particularly where the subject has a known risk of developing an acute respiratory condition. The microprocessor may therefore be programmed with instructions that, when executed, cause it to:

Perform feature e.i. by collecting from the sensor a signal relating to each breath taken by the patient; and ii. accumulating and store data from collected signals;

Perform feature e.ii. by inputting the data to a machine learning module running on the processor at a first level of intensity;

Perform feature e.iii. by screening the most recent signal collected for a respiratory anomaly in the patient's breathing;

submitting received and computed components to a machine learning algorithm—the machine learning algorithm may be running at relatively low level of frequency, such as once or less than once per breath cycle (i.e. periodically and/or at a frequency dependent on the severity of the subject's respiratory condition—

6 e.g. once or more per breathing cycle when an impending condition is predicted or the subject's severity increases); and Perform step e.iv. by causing the module to be run at a second, relatively elevated level of intensity compared with the first level, if screening indicates an anomaly;

testing the anomaly against pre-set alarm criteria indicative of the anomaly being a precursor to an acute condition being imminent; and output an alert if an alarm criterion is met.

In some embodiments, step e.iii may involve receiving an output from the sensor corresponding to the future cycle, and comparing the prediction with the output corresponding to the future cycle.

Preferably, the predictive numerical model comprises extended Kalman filtering (EKF) performed on a component of the sensor output.

Further preferably, the processor is programmed to perform principal component analysis (PCA) on the sensor output to identify the component on which to perform the EKF.

In the device, the processor may be programmed to perform EKF on the identified principal component only.

In a preferred embodiment, the future cycle is the next cycle after the most recently observed cycle.

In a further preferred embodiment, the sensor output relates to an acoustic signal detected in the functioning of said physiological system.

In a preferred form of the invention, the response comprises executable instructions causing the sending of data used in the comparison to a machine learning model and causing the model to consult a database of historical output and predictions for determining whether the comparison indicates an acute condition is imminent.

In a further preferred form of the invention, the processor is configured to allocate increased processing resources to running the machine learning model when the comparison yields a disparity between the prediction and the corresponding event in said future cycle.

In the event an acute condition is indicated, the processor preferably outputs an alert signal for receiving by the patient and one or more of carer or medical practitioner of the patient.

Preferably, the alert signal comprises haptics.

The processor may be programmed to subject the sensor output to preliminary filtering before performing said principal component analysis.

The physiological function responded to by the device preferably concerns a respiratory system function. The acute medical condition may relate to a chronic respiratory disease or medical condition which includes but is not limited to asthma.

In a preferred embodiment, the sensor comprises acoustic sensing means configured for receiving frequencies characteristic of inflammation signs within the upper respiratory tract of the patient. The frequencies may correspond to known wheeze frequencies.

According to a third aspect of the invention, there is provided a method of anticipating an acute medical condition in a prospective patient having a known risk of developing such condition, the method comprising steps of:

a. providing a patient with a wearable device having on board a sensor and a signal processor connected in data communication;

b. operatively applying the device to a selected portion of the patient's skin;

causing the processor to:

i. collect from the sensor a signal relating to (e.g. for) each breath taken by the patient;

ii. isolate and store a principal component of each signal—this may involve isolating and storing, for each breath, a principal component of the respective signal. Moreover, the original signal itself may be stored;

iii. utilise at least one stored principal component in generating a prediction of a principal component of a future signal relating to the next expected breath of the patient;

iv. isolate from the patient's next breath an actual principal component thereof (this may involve collecting from the sensor a signal relating to the patient's next breath);

v. determine the variance between actual and prediction; and vi. if the variance exceeds a pre-set limit, output an alert of an imminent acute condition arising.

Preferably, the method includes causing the processor to store the predicted and actual components.

In an embodiment, the method includes causing the processor to store the signal.

The method may further include providing a machine learning module operable to utilise the predicted and actual components as inputs.

The machine learning module is preferably activated when the variance approaches the pre-set limit.

The method may include causing the processor to determine the variance limit based on stored component values. In a preferred form of the invention, the method includes causing the processor, on determining a variance approaching the pre-set limit, to enter an enhanced mode of operation. The enhanced mode of operation preferably includes the step of increasing signal sampling rate.

The step of generating the prediction preferably includes applying a Kalman filtering process to the stored components.

The filtering process is preferably Extended Kalman filtering.

According to a fifth aspect of the invention, a wearable medical condition anticipation device comprises a microprocessor in data communication with a sensor selected to collect a signal relating to respiratory function of a patient having a known risk of developing an acute respiratory condition, the processor being programmed to execute instructions causing it to:

i. collect from the sensor a signal relating to each breath taken by the patient;

ii. accumulate and store data from collected signals;

iii. input the data to a machine learning module running on the processor at a first level of intensity;

iv. screen the most recent signal collected for a respiratory anomaly in the patient's breathing;

v. submit received and computed components to a machine learning algorithm running at relatively low level of frequency;

vi. if screening indicates an anomaly, cause the module to be run at a second, relatively elevated level of intensity compared with the first level;

vii. test the anomaly against preset alarm criteria indicative of the anomaly being a precursor to an acute condition being imminent—alarm criteria may be set according to any desired regime, or based on confidence that a breathing state change is indicated (e.g. regarding "regime", the alarm may sound if the expiration period shortens by a predetermined amount and, regarding "confidence", the alarm may sound if it is determined with a predetermined confidence that the subject's breathing has moved from Zone 1 into Zone 2—see FIG. 1); and viii. output an alert if an alarm criterion is met.

According to a sixth aspect of the invention, a method of forestalling an acute medical condition comprises steps of:

a. providing a prospective patient having a known risk of developing such condition with a wearable device having on board a sensor and a programmed signal processor connected in data communication;

b. operatively applying the device to a selected portion of the patient's skin;

c. causing the processor to:

i. collect from the sensor a signal relating to each breath taken by the patient;

ii. accumulate and store data from collected signals;

iii. input the data to a machine learning module running on the processor at a first level of intensity;

iv. screen the most recent signal collected for a respiratory anomaly in the patient's breathing;

v. submit received and computed components to a machine learning algorithm running at relatively low level of frequency;

vi. if screening indicates an anomaly, cause the module to be run at a second, relatively elevated level of intensity compared with the first level;

vii. test the anomaly against pre-set alarm criteria indicative of the anomaly being a precursor to an acute condition being imminent; and viii. output an alert if an alarm criterion is met.

The screening step may involve predicting the signal for the next breath and testing the accuracy of the prediction against the actual signal when received.

According to a seventh aspect of the invention there is provided a personal medical assistant comprising means for providing a user, who suffers a chronic respiratory condition characterised by acute symptoms, a symptom-free (or symptom minimal) life, the means comprising a wearable sensor operatively configured to feed physiological function data to a processor which is programmed to analyse the data for detecting a component which is an indicator of an imminent avertable acute medical condition relating to said chronic respiratory condition, the analysis including a predictive numerical process and comparing a future prediction of a cyclical signal with the signal when observed.

Preferably, the means further comprises an inhaler device chargeable with medication for dosing the wearer of the sensor. Further preferably, the inhaler device comprises actuation means operable by the wearer to dispense medication in an effective dose for addressing the medical condition, the actuation means being in communication with the processor for logging details of the dispensing event.

It is an object of this invention to address the shortcomings of the prior art and, in doing so, to provide an early anticipation system for treatable conditions having acute symptoms, such as asthma, early anticipation facilitating the provision of suitable remedies at an early stage in the development of the symptoms.

A further object of the invention is to provide a method of assisting a sufferer from a chronic medical condition to avoid acute symptoms of such condition.

A technical challenge to be overcome is that of utilising readily detectable, but noisy (polluted, non-ideal, real world data) acoustic signals to detect asthma signs before they become symptoms. Here "symptoms" refer to easily noticeable pointers that indicate the on-set symptoms for the patient. The identification of symptoms may be at a comparatively advanced time in the onset of an asthma attack, when compared with detection of "asthma signs" as that term is used in the present context.

BRIEF DESCRIPTION OF DRAWINGS

In order that the invention may be readily understood, and put into practical effect, reference will now be made to the accompanying figures. Thus.

DETAILED DESCRIPTION OF AN EMBODIMENT OF THE INVENTION

Embodiments of the invention will now be described with reference to an asthma management system, such as system 10 of FIG. 2. The system may track and/or record a user's respiratory health. The system employs data filtration and processing techniques to help detect foreseeable adverse events, such as chronic symptom development—e.g. asthma attack. The system may also employ machine learning for this purpose.

The system may provide advance warning of the onset of an adverse event. The system may thereby enable pre-emptive, or at least timely, remedial action to ward off or alleviate the adverse event—e.g. an asthma attack.

The system can operate in a normal mode and an elevated mode. In such embodiments, the system may remain in the normal mode of operation until the system determines a subject (e.g. a patient) is at risk of suffering an adverse condition. For example, based on current sensor measurements, from sensor(s), of a subject's respiratory or other physiological system, the system may predict a sensor measurement subsequently expected. The system receives the subsequently expected sensor measurement from sensor(s) and compares it to the prediction. Based on that comparison, the system determines if the subject is stable and, if so, remains in the normal mode of operation. The system enters the elevated mode in the event of attack precursors being identified—e.g. if the comparison suggests an adverse condition is imminent. In elevated mode, machine learning is implemented to confirm determinations made in the first, normal mode of operation.

Figure 1:
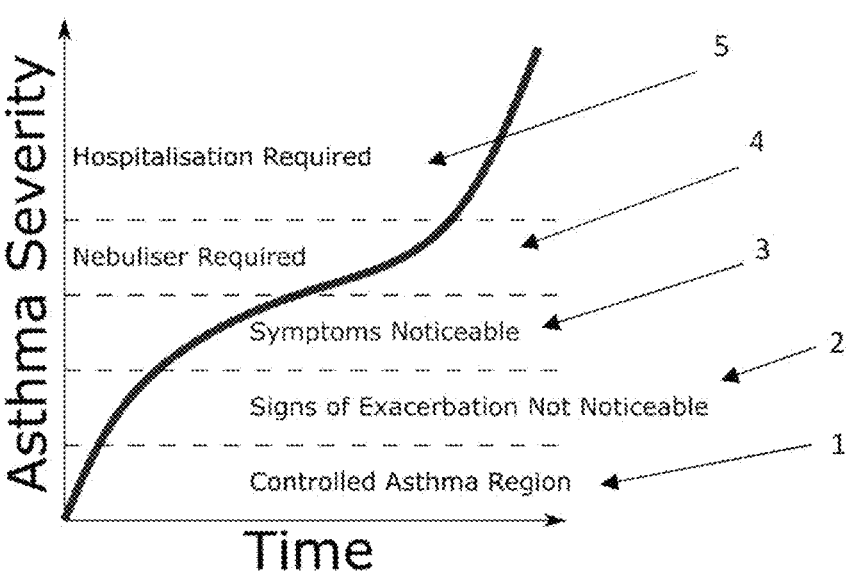
FIG. 1 is a graph showing the categories of severity of asthma symptoms and a plot of the degree of typical severity experienced by a sufferer over time.

In an example of use, the system may use respiratory parameters—e.g. respiratory rate, respiration period, or inhalation and/or expiration timing or ratio—to predict what the next respiratory parameter should be for the subject to maintain a stable condition or the subject's current severity—ref FIG. 1. If the system determines the next respiration event is comparable to the prediction—e.g. the same or within a predetermined period/threshold of the prediction—then the system remains in the normal mode of operation. Otherwise, it enters the elevated mode of operation. In some embodiments, to reduce false alarms, the prediction may be performed repeatedly for a predetermined number of cycles of the physiological system—e.g. predetermined number of respiration events for the respiratory system—before the system enters the elevated mode of operation, or before the system generates an alarm/feedback.

In the event of the identification of the potential onset of an adverse event, the system 10 may provide haptic or kinaesthetic feedback or communication—e.g. through alert 24. Such feedback involves applying forces, vibrations, or motions to the user. It also involves using touch sensors to receive feedback from a living organism. Alert 24 may also, or instead, involve generating and sending a digital alert such as a voice call with digital recording, text message, and chatbot interface. The voice call and text message may be stand alone and simply contain information relevant to the condition and subject—e.g. likelihood of onset, location of patient, type of condition and so forth. The voice call and text message may instead permit prescribed responses to allow the recipient of the call or message (e.g. subject, their clinician or carer) to interact with the system 10 to gather further information. Similarly, the chatbot interface may be produced on a smartphone and enable the recipient of the alert to interact with the chatbot to gather information relevant to the condition and subject.

The present system also uses a Kalman filter, being a computational model applied in robotics fields. Kalman filters are suitable for applications where a series of measurements of a dynamic system (e.g. the patient's respiratory system) have been taken over time, and only uncertain information is available about the current state of that dynamic system. The Kalman filter therefore uses the series of measurements, and the uncertain information, to make an educated guess about what the system is going to do—e.g. the state it will next be in. In the present context, Kalman filtering may be used to infer whether the patient is currently experiencing normal or abnormal—e.g. adverse—respiratory conditions. Kalman filtering may be used for many applications including filtering noisy signals, generating non-observable states, and predicting future states. The predicted future state—i.e. the state predicted for the future cycle for which the prediction is being made—may be a predicted to be a pre-attack (e.g. asthma attack) or during attack state and, as such, an alarm may be raised per box 54 of FIG. 3 if the future cycle (i.e. the sensor output corresponding to the cycle for which the state has been predicted) is the same as, or within a pre-set limit or threshold of, the prediction. Alternatively, the predicted future state may be a predicted to be normal breathing or recovery/post attack in which case the alarm raised per box 54 of FIG. 3 may be cancelled or otherwise not raised if the future cycle is the same as, or within a pre-set limit or threshold of, the prediction. If the future cycle is outside the pre-set limit or threshold then the alarm may be raised or maintained as the case may be.

The Kalman filter operates on two types of equations: prediction equations and update equations. The prediction equations predict the current state of a system, based on the previous state and the commanded action. The update equations look at a system's input sensors, the level of trust for each sensor, and the level of trust in the overall state estimate. This filter works by predicting the current state using the prediction equations followed by checking how good of a job it did predicting by using the update equations. This process is repeated continuously to update the current state.

An Extended Kalman Filter (EKF) applies prediction techniques in a nonlinear system. It therefore requires preliminary linearization of the system model in question. This may require implementation of a Jacobian, which allows different values to be scaled differently. The second and easier approach is to use piecewise approximation, in which data is broken down into regions that are close to linear and form different A and B matrices for each region. This allows checking of the data and use of the appropriate A and B matrices in the filter to accurately predict the system transition state.

The graph in FIG. 1 provides a curve that is a plot of severity of an asthma attack against time. The curve begins at the origin and passes through zones of increasing severity, distinguished by means of the stippled lines extending horizontally from the Y axis. The zones require corresponding increasingly drastic medical intervention as asthma severity increases. The system outputs a representation of the graph, showing a carer or assistance giver where the wearer of the device is on the curve. For example, a parent will be able to see immediately the bracket in which their child is suffering at any given stage of an attack. Children often dismiss or ignore their own noticeable symptoms until a stage of severity that requires nebulisation is attained. A parent may also miss an early sign of an impending attack. Once symptoms develop to be observable, parents will attempt remedies from the "symptoms noticeable" middle region 3 and are likely to end up nebulising too late, with serious consequences, for example hospitalisation (stage 5). The present invention enables a response to be implemented in the initial stages, in the regions marked 1 (most preferably) and 2.

The zones 1 to 5 in the graph in FIG. 1 are determined in accordance with the Acute Asthma Exacerbation Intensity Research Score (AAIRS—i.e. the Y-axis "Asthma Severity" is AAIRS Asthma Severity). The criteria that are measured to distinguish between zones that are used by the system 10, described in FIG. 2, will be those that the sensors are capable of measuring—these may either be some or all of the criteria used in the AAIRS assessment, or criteria (such as audio features measured by acoustic sensors) the efficacy of which has been assessed against, e.g., AAIRS assessment. For example, where an acoustic sensor is used, the signals will be audible to the sensor or, where breathing has stopped entirely, inaudible or otherwise measured as an absence of normal audible signal.

The system, in an embodiment, includes a software application ("app") configured for receiving operational data relating to the severity as shown in FIG. 1—e.g. the result of comparison between the predicted and actual sensor measurements of the physiological system of the subject—and executing instructions to provide responsive prompts to the user or a designated carer, for example reminders about administering a medication. The system may output, for example, the graph shown in FIG. 1 and identify where the subject's current severity level lies on that graph, or output the zone in which the subject's current respiratory condition lies and/or a description or alert relating to that zone. The system may send an output to a smartphone for display of the current severity level of the subject and/or to provide responsive prompts such as prompting the user or a carer to nebulise, or to alert emergency services.

The system hardware includes a programmed smartphone running the app, and a near range wireless communications device operating according to a protocol such as the well-known Bluetooth® protocol. Connectivity may alternatively be affected by other suitable known means, including over a mobile telephone or Wi-Fi communications network.

The system further includes a wearable device in the form of a patch and a docking station, at which the device may be docked for battery recharging. Preferably, the docking station is configured to relay medically relevant data to the wearer, for example weather conditions and forecasts, as well as measured and expected pollution and pollen levels. Relays may be affected by visual interface, audio message and the like. The station may further be configured to prompt for and receive inputs from the wearer concerning their medication usage. The inputs are logged for later reference. The prompts may be communicated via voice message, as may be the wearer's responses.

Figure 2:
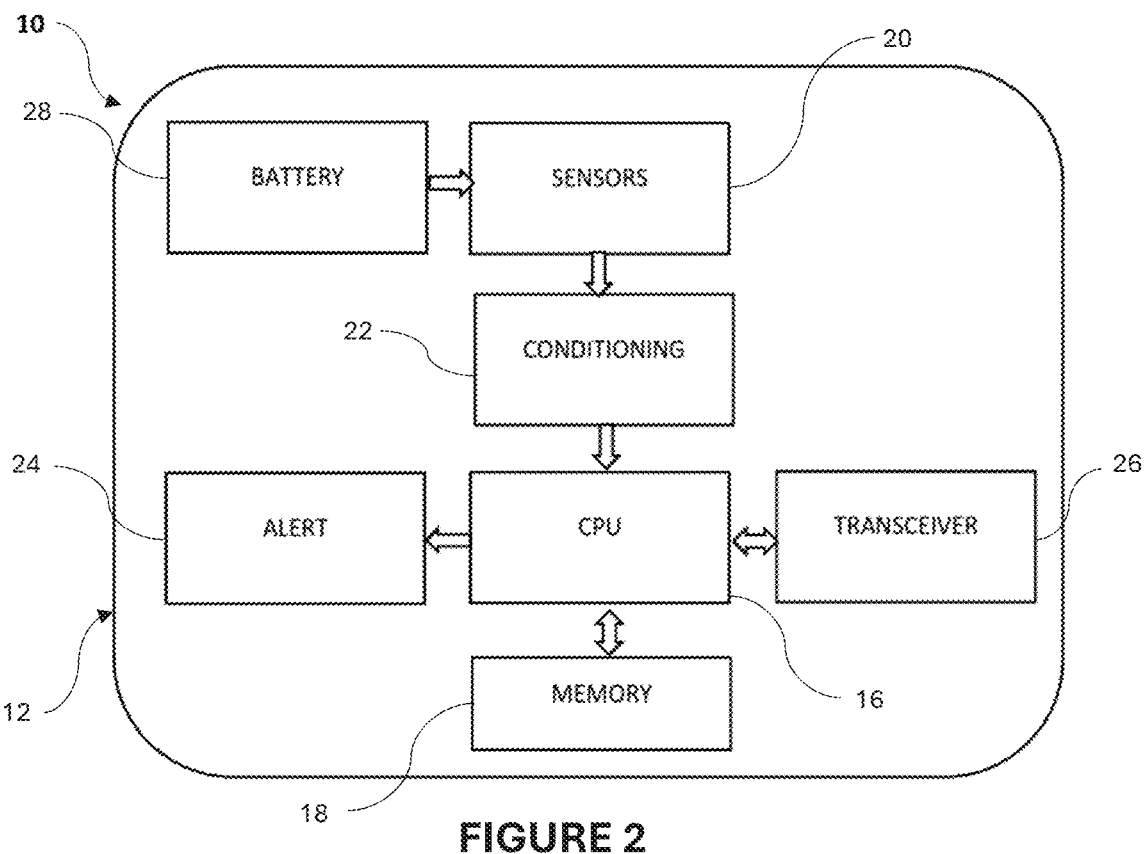
FIG. 2 shows in schematic form a diagram of a preferred embodiment of the device of this invention.

The wearable device, being in the form of an adhesive patch in this exemplary, non-limiting preferred embodiment, is represented schematically in FIG. 2 and is denoted by the numeral 10. It comprises a moulded plastics housing 12 having a rear surface 14. The rear surface is rendered adhesive for application on the user's skin, by applying to it a sheet of medical grade silicone. It is temporarily removable and washable to restore adhesiveness. If it becomes unserviceable, it may be replaced separately from the housing. Functional electronic components are sealed within the housing. They are operatively connected as described below.

Figure 4:
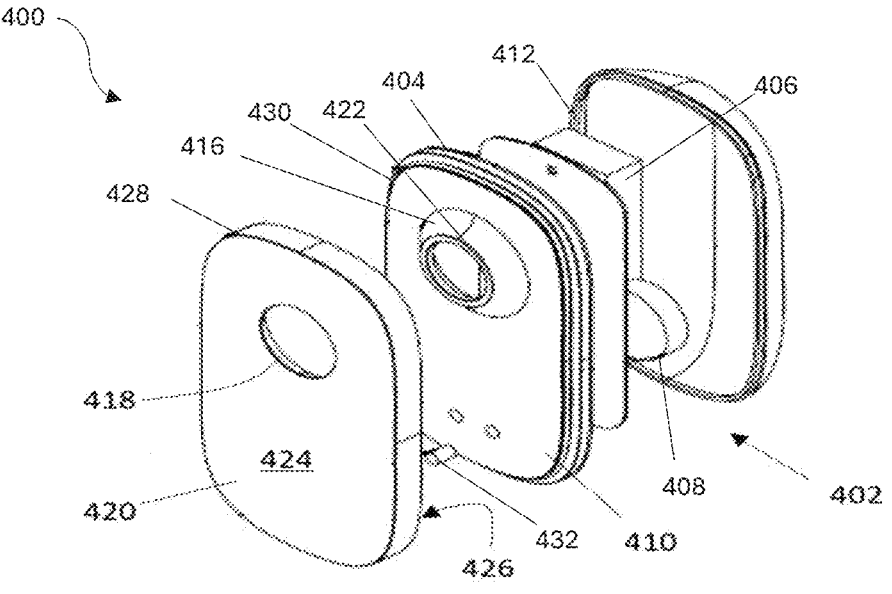
FIG. 4 is an exploded view of a device such as that shown schematically in FIG. 2.
Figure 5:
FIG. 5 is an assembled view of the device of FIG. 2, with the adhesive patch separated.
Figure 6:
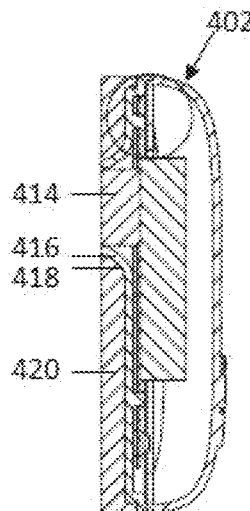
FIG. 6 is a longitudinal cross-section view of the device of FIG. 4, in an assembled condition such as shown in FIG. 5.

A device, such as the embodiment 400 shown in FIGS. 4 to 6, may be a wearable patch. Where the sensors are acoustic sensors, the patch may act like a wearable stethoscope. Having the nature of a stethoscope (i.e. for registering acoustic signals), the device may sit on the chest and record airflow acoustics in the lower airways. The wearable chest patch then will be able to provide live feedback and alerts to a parent, guardian or caregiver—e.g. via an app installed on their smartphone—to help them monitor a patient's asthma. The smart phone app will send alerts if there are signs of an asthma exacerbation (i.e. a worsening of condition) and has the potential to allow the parent, guardian or caregiver to make informed decisions with regards to management and treatment.

Audio signals of a patient's breathing are collected through an acoustic sensor/monitor patch (see sensors 414 in FIG. 6) held to patient's upper chest area. The monitor patch consists of a miniaturized condenser microphone and accompanying electronics. The patch may be tethered to a computer via a USB cable. The cable provides power and data transmission. The tether may be in place during recording so the computer receives, in real time, recordings from the patient. Alternatively, data may be stored in memory (see PCB 404, including memory, in FIG. 4) and periodically sent wirelessly, or via wired connection, to the computer.

The patch is held onto the patient via double sided body tape (e.g. adhesive patch 420 of FIG. 4) which is a commercially available biocompatible material. Only the double sided tape is in direct contact with the patient's skin and is disposed of after each single use. The monitor housing (e.g. housing 402 of FIG. 4) is made of 3D printed ABS which is cleaned with an alcohol wipe after each use. Data will be labelled with patient's unique identification code and generally not with patient names.

With particular regard to the embodiment shown in FIGS. 4 to 6, device 400 comprises a housing 402, printed circuit board (PCB) 404, battery 406 and alert component 408. The housing 402 is formed from a base part 410 and upper part 412 that engage—e.g. using a snap-fit or interference fit in a known manner—to seal the PCB 404, battery 406 and alert component 408 in the housing 402 as shown in FIGS. 5 and 6. The PCB 404 may comprise the transceiver, CPU, conditioning module and memory of the device of FIG. 2. The alert component 408 may comprise a vibration component through which the device 400 can indicate, via vibration, to the wearer (i.e. the subject) that an alert condition has been identified—e.g. that an acute medical condition is impending.

The housing 402, presently the base part 410 thereof, supports the sensor(s) 414 (see also sensors 20 of FIG. 2). The sensor(s) 414 are received in a protrusion 416 when the housing 402 is in an assembled condition as shown in FIG. 6. The protrusion 416 of the base part 410 is received in a corresponding recess 418 of an adhesive patch 420. The recess 418 is shaped to cooperate with the shape of the protrusion 416. The depth of the recess 418 through the adhesive patch 420 is substantially the same as the height of the protrusion 416. As such, when the adhesive patch 420 and housing 402 are engaged, a lower face 422 of the protrusion 416 is substantially coplanar with the base 424 of the adhesive patch 420 when it is in contact with the skin of the subject. This ensure the sensors 414 are as close as possible to the subject during use.

To maintain connection between the adhesive patch 420 and housing 402, both the base 424 and top surface 426 of the adhesive patch 420 are adhesive—the skilled person will appreciate the adhesives used in this circumstance result in adhesion that can readily be broken when intended and, as such, no permanent bonding with the skin of the patient occurs. Moreover, one of the adhesive patch 420 and housing 402 comprises a lip 428 adapted to be received around a raised portion 430 of the other of the adhesive patch 420 and housing 402. Presently, the adhesive patch 420 comprises the lip 428 and the housing 402 comprises the raised section 430. Thus, the lip 428 restricts relative lateral movement between the adhesive patch 420 and housing 402. In addition, the housing 402 further includes a prong 432 that is received in a corresponding bore (not shown) in the adhesive patch 420. The prong 432 further restricts relative movement between the adhesive patch 420 and housing 402.

A central processing unit/processing unit (or CPU) 16 is connected to transfer data to and retrieve data from a memory module 18 and to receive inputs from a sensor unit 20 via conditioning electronic circuitry 22. The sensor unit 20 is located behind, and generally adjacent to, the medical grade silicon to be as close as possible to the skin of the subject when the device 10 is placed thereon.

The processor sends outputs to an alerting device 24. It is also connected to a wireless transceiver 26. The power source for the components is a battery 28.

Sensor unit 20 comprises an acoustic pickup or sensor locatable against the wearer's skin. Any suitable pickup may be employed. Piezo-electric pickups are preferred in some embodiments, and micro-electromechanical systems (MEMS—e.g. such as that used in cochlear implants) may be used in other embodiments. The sensors are selected and configured for picking up wheeze frequencies or other signs of inflammation in the respiratory tract.

Alerting device 24 generates haptic output that provides physical stimulation to the wearer if imminent worsening of their medical condition is predicted. By way of non-limiting example, the physical stimulation may be in the form of live haptic feedback to the wearer. Suggestions, which may not necessarily be restricted to the medical field, are generated by the app and outputted via the smartphone to help the user stick to their personal asthma plan. The suggestions may be communicated by text message, an automated telephone call, or an audio file for automatic playback.

Software executing on processor 16 via the sensor unit (e.g. comprising the acoustic sensor), enables detection of changes in the wearer's regular breathing that signal an unexpected or unhealthy condition developing, for example in the upper respiratory tract. For example, the software executing on processor 16 may determine a time period for the exhalation portion of a breathing cycle, or a time for both the exhalation portion and the inhalation portion, using an acoustic (i.e. audio) signal from an acoustic sensor. If the exhalation portion shortens and/or the noise volume of the exhalation increases (e.g. wheezing or rasping), this can indicate that respiration is become more difficult. For example, if the exhalation portion of the breathing cycle shortens, this can indicate that the airway has constricted or contracted, which causes mucus generation which speeds breath outflow and causes wheezing. Therefore, the system 10 can use an acoustic sensor positioned on, for example, the torso or back of the subject to monitor for airway contraction and shortness of breath, from which it can determine if the subject is at risk of developing an adverse condition—e.g. asthma attack.

In one embodiment, the system 10 comprises an acoustic sensor for collecting an analog sound of the subjects breathing. The analog sound is converted into a digital signal that is representative of the subject's respiratory signal at the time of collection. The digital signal can then be processed with a variety of standard signal processing tools such as time domain transforms, principal component analysis and/or a combination of tools. Several concurrent determinations for abnormalities in breathing can be made, including drastic changes from one breathing cycle to the next, typical precursor signs for mucus build up such and/or muscle constriction such as inhalation exhalation ratio, wheezing, coughs and pops. A drastic change may be, for example, where inhalation or exhalation, or the ratio therebetween, varies unexpectedly by over 10% (or any other desired threshold).

In this way, the patch 10 can operate as a wearable stethoscope for listening to lung function. Accordingly, the acoustic sensor(s) can directly measure sound from the subject and, from that sound, determine respiration parameters. Therefore, the acoustic sensor(s) 20 avoid the need to determine respiration parameters using a proxy measurement—e.g. of heart rate—and inference of the respiration parameters represented by the proxy measurement.

In addition, where a docking station or smartphone is used, the docking station or smartphone may collect air quality data (e.g. from an online source) and send the air quality data to the patch 10. Preferably, the air quality data is for air in the vicinity of the subject. The air quality data can then be augmented with data from sensor(s) 20 to improve accuracy and reduce false alarms. For example, when air quality is good, some changes in respiration characteristics or parameters may indicate that the subject is playing sport. Accordingly, the system may not respond. Where air quality is poor—e.g. high pollution or pollen levels—the system may raise an alert despite the physiological system (e.g. respiration system) having substantially the same parameters (e.g. respiration rate, exhalation period) as when the subject is playing sport in good quality air.

An accelerometer or clock may be built into the patch 10 and/or the system may be in communication with a smartphone accelerometer or clock, to further reduce false alarms. For example, if a subject normally goes for a run at a particular time of day, then respiration may be faster over that time of day and the system may respond differently than at other times of day. In this regard, since the system may determine whether or not to alert the user or their carer based on measurements of the physiological system exceeding a predetermined threshold—e.g. 20 breaths per minute—the system may initially send alert messages to the subject via their smartphone when the respiration rate exceeds that threshold. If the subject consistently clears the alert at a particular time of day—e.g. by pressing a "Clear alert" button on a smartphone touchscreen—then the system may learn that, at that time of day, the threshold must be adjusted so that alerts are not unnecessarily raised. The system can similarly learn to avoid using a baseline (i.e. expected 'at rest' activity of the physiological system) and predetermined threshold measured during sleep, as the baseline and threshold against which sensor measurements are compared during the daytime. Alternatively, based on accelerometer measurements, the system may raise the threshold if it appears the subject is exercising. Once the time of day passes, or the exercise ceases, the threshold may be reverted back to its original level.

The system 10 comprises memory 18. Memory 18 may store historical data—e.g. sensor measurements—to facilitate longitudinal study or learning of the subject's physiological health. A machine learning algorithm executed by the processor 16 may run on the historical data to determine changes in system behaviour. Some examples are as set out above, for adapting system behaviour at different times of day or during periods of higher and lower activity—e.g. exercise. In addition, the machine learning algorithm may identify that, over time, the subject's physiological system is changing. For example, the subject may have had a respiratory rate of 12 breaths per minute, or an exhalation period of 3 seconds per breath. Over an extended period of time—e.g. 2 months—and with only minor variations in the respiration rate or exhalation period, the subject may progressively tend towards 15 breaths per minute or an exhalation period of 2 seconds per breath. This may indicate progressive worsening of the subject's respiratory system or of the environment around the subject—e.g. in the case of a mine or chemical plant worker, where particulate and noxious gases in the air can produce adverse effects in the respiratory system.

In such cases, the system may set a threshold defined by worsening condition—e.g. increasing the baseline respiration rate to 16 breaths per minute. Rather than producing an alert if the next sensor measurement is outside the predetermined threshold from the predicted sensor measurement, the system may produce an alert if the next sensor measurement is within that threshold.

Figure 3:
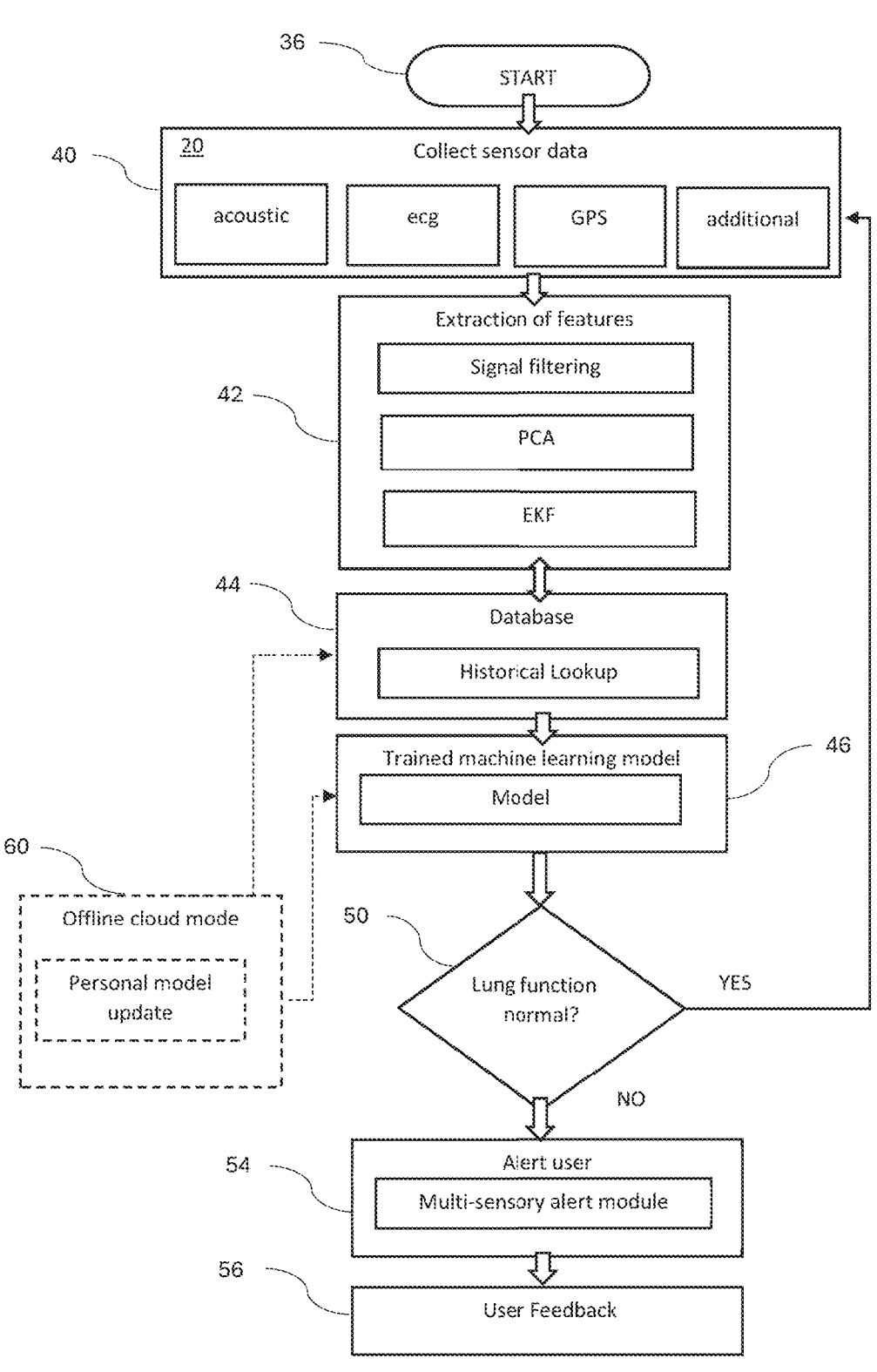
FIG. 3 is a schematic diagram of the system logic applied when a device of FIG. 2 is applied in a monitoring process of the invention.

Referring to FIG. 3, the logic of the system in this preferred embodiment is demonstrated with reference to patch 10 of FIG. 2. The system employs a two-mode method to determine the current breathing state of a user with asthma and to predict the occurrence of asthmatic events. The first step is an Extended Kalman Filter (EKF) configured to predict the next inspiration or exhalation signal. When a signal not related to healthy regular inspiration or expiration is detected, the system enters high awareness or elevated mode. The system awareness—i.e. sample resolution or sample rate—is increased during the second step, to facilitate machine learning.

In this embodiment, once the system is activated (at step 36), the sensor unit 20 collects and feeds condition-related data to the conditioning electronic circuitry 22. Every breath taken by the wearer includes a period of inspiration and of expiration which are detected and captured (e.g. stored in memory), using the sensors in the sensor unit.

As noted, the sensor unit can be sensor-agnostic and, in this embodiment, comprises not only an acoustic sensor, but also an electrocardiogram (ECG) sensor and a location sensor (GPS). Additional sensors may be included to obtain data of other physiological conditions of the wearer of the patch. In some cases, a temperature sensor, or a skin surface moisture sensor may be deployed—e.g. a temperature sensor may monitor the temperature of the exhaled breath of the subject and record changes in the temperature of the subject's exhaled breath. An increase in temperature may be used as an indication of increased blood flow to the lungs. Increased lung blood flow may be caused by inflammation from respiratory distress such as asthma.

The sheets defining the surfaces of the patch will be adapted according to the requirements of the sensors being deployed, for example to allow direct skin contact through apertures where needed. The sensor-agnosticism in this invention is enabled due to the nature of observations and confidence values in Kalman filters acting on the sensor outputs. Kalman filters use a series of measurements taken over time, to probabilistically determine unknown variables such as, in the present context, the next sensor measurement or a sensor measurement taken at some future time.

The raw sensor signals from an inspiration or expiration event often require pre-processing to remove signal noise, unnecessary data and other impurities or unwanted signal artefacts. At step 42, the processor performs signal rectification and filtering routines on the raw signal data according to known methods. These methods may include signal transformation—e.g. to an appropriate domain—in certain cases, when warranted. The resulting cleaner signals then undergo principal component analysis (PCA) for extracting the signal vectors of most significance.

In the PCA step, the filtered signals are processed separately for each sensor. The filtered signals are broken into their principal components, based on variance, according to known methods. In this embodiment, the signal is an unbroken string of ten or more readings, generally taken from a single sensor (fewer than 10 readings may be used as appropriate for a particular analysis). The strings are formed by sliding a window over the sensor measurements, such that the same measurement can appear in multiple strings—e.g. for measurements 1, 2, 3, 4, 5, and a sliding window of three, one string may have measurements 1, 2, 3 another string may have measurements 2, 3, 4 and so on. Strings of other lengths may be selected. Significance of a vector produced by PCA may be determined with the help of historical data 44 and learning accumulated for the user in question (at step 44). The most significant vectors are logged in on-board storage chip in memory module 18.

The historical data may be historical output from the sensor of the device in question, or from previous measurements taken by other devices. For example, the historical data may include clinical pooled data including labels for typical respiratory anomalies that indicate the onset of a respiratory condition. Alternatively, the historical data may constitute prior recordings for the particular patient. This would then cause the assessment/comparison to take into account the specific respiratory condition of the patient in question—e.g. smoker status, age, nasal or oral breathing, etc.

The storage chip is used also to retain the predicted inspiration and expiration signals obtained from the Extended Kalman Filter (EKF) discussed below. Where storage capacity is available, the raw signal from which processed output is derived is also stored.

The processor applies EKF to the principal vectors isolated by means of PCA as a screening step. The memory 18 may be used to store or log the most significant vectors and predicted inspiration or expiration signal from the PCA and EKF respectively. The EKF is configured to predict, from the data of the most recent inspiration or expiration event of the patch wearer, the signal or signals that should characterise the next such event. In accordance with EKF protocols, each sensor employed in the sensor unit is assigned a confidence value, based on signal quality and relevance in a known manner. The EKF combines and manipulates input signal data, from which it predicts the values of the next inspiration or expiration signal and the vectors therein.

The actual signal/s obtained from the next event are then compared with the predicted signal. The variance is computed. If a patch wearer who, according to their most recently monitored breathing event (e.g. a sensor measurement of a single respiration event, or a sensor measurement in the form of a string as discussed above, which may include multiple respiration events), is in a healthy respiratory state, returns, as their next actual signal, one that constitutes an anomaly in not being consistent with healthy regular inspiration or expiration, the system is triggered to enter a mode of elevated operational awareness. An anomaly may be defined by the variance reaching or exceeding a pre-set or predetermined threshold—e.g. where an exhalation period of 3 seconds is predicted, or a predicted ratio of the times for exhalation to inhalation is 3:2, the threshold may be an exhalation period of 1.5 second or a ratio of 3:4.

In such elevated awareness mode, the system invokes a machine learning (ML) algorithm 46, which is a reinforced supervised anomaly detection model trained from clinical data. The trained/ML model is used in the patch or device applied to skin of the user (e.g. patient or subject) to classify the breathing state of the user. The states are: normal breathing, before asthmatic event, during asthmatic event and after asthmatic event. The algorithm ML model thus uses current and historical data (including labelled data that has been labelled based on the state it indicated, whether it was an indicator of the impending onset of an acute medical condition, whether it was an indicator for impending recovery from an acute medical condition or other labels), which may also include principal components (PCs) of that signal data, to determine the users breathing state—e.g. by comparing a sensor measurement (i.e. signal) to the labelled data and determining the state of the subject by reference to the label applied to the data that most closely approximates the signal using known methods—e.g. PCA. In the case that irregular breathing is detected 50, additional data such as the machine learning output and user feedback 56 (e.g. 'Clear alert', 'Contact carer' or 'Contact emergency services') will also be logged. This additional data can then be fed into the ML model. The machine learning algorithm may be consistently re-deployed—e.g. each time the system enters the elevated mode of operation—to better fit the individual's condition.

When the system is in high awareness mode, more historical data is used, this increases the computational time while increasing accuracy. When abnormal breathing is detected and the system moves into high awareness or elevated mode, an alert is sent to the user. For example, the patch may vibrate and flash an LED. After an alert is sent the user is prompted to verify the alert. This information is logged in the database for later machine learning algorithm improvement. Normal monitoring is resumed in power efficiency mode after the alert is sent. Moreover, a new alert may not be sent until a specified amount of time has passed after the previous alert was sent. If the subject does not clear the alert, or the system determines the adverse condition has worsened, smartphone alerts may be sent to any registered phones (e.g. phones identified in the subject's smartphone as being phones to contact in the event of an emergency, or emergency services), the alerts containing location information and the type/severity of the adverse condition. This information can be used to locate the user and/or call for medical assistance. High awareness mode should not be consistently used as it slows sampling time and creates additional heat from the CPU.

When the system determines normal breathing state has resumed, the system should return to gather sensor data in the normal mode of operation. The lower data requirements result in the normal mode being power efficient when compared with the elevated mode of operation, and result in reduced computational time and CPU load.

The trained model is used to categorize the state of the user's lung function. The categories of state are defined as: normal breathing (e.g. inhalation and exhalation periods are in a ratio that is healthy for patients); before an asthmatic event (e.g. some increase in exhalation period when compared with inhalation period); during the asthmatic event (e.g. significantly increased exhalation period when compared with inhalation period); and after the asthmatic event—this will be determined as subsistence of the abnormality observed on the signal (e.g. acoustic signal) or breathing exhibiting the characteristics of recovery as discussed with reference to FIG. 1. The system may respond to each category, or level of severity, differently—e.g. not respond to normal breathing, respond to the 'before an asthmatic event' category by alerting the subject, respond to the 'during asthmatic event' by alerting emergency services, and so on. The trained model makes use of current and historical data 44 to determine the patch wearer's breathing state.

The latest observed respiratory signals from the patch sensor are tested or compared against the trained model's output. If a patch device wearer returns a signal that is consistent with the predicted signal obtained from EKF, this represents a nonthreatening condition, and control is transferred back to signal-collecting step 40.

If the latest observed (i.e. measured or sensed) signal shows a statistically significant variance from the signal predicted, it is flagged for later use in the machine learning aspect of the system. In this context, 'statistically significant' may mean within 10% of the value of the predicted next sensor measurement, within a predetermined threshold of the value of the predicted next sensor measurement, or any other desired mechanism for asserting the actual next sensor measurement does or does not sufficiently represent the value of the predicted next sensor measurement.

Respiration events continue to be monitored as before, but an alert is triggered 54 using output device 24. The output device may be one or more of a vibration pad, an audible output device such as a loudspeaker, and the like. In addition, the transceiver is programmed to broadcast, using known wireless communications means, a wireless signal to one or more user-selected mobile communications devices, such as mobile telephone handsets associated with the wearer's carers, parents and the wearer himself. The signal may be adapted for warning the users of the handsets of the impending anticipated condition of the wearer and the need for intervention. The transceiver may be programmed further to provide a setting whereby the wearer may elect that in the event of a medical event being signalled, the transceiver broadcasts an alert to the geographically nearest of a group of wearer preselected contact persons, or to persons within a given range of the wearer. The determination of proximity is made using global positioning co-ordinates received as inputs to the app from the handsets of persons designated by the wearer and of the wearer's own handset. The wearer is given the option of selecting the medium by which the alert should be issued: for example, by way of an in-app notification, text message, social media-based messaging app, or telephone call. In the event that no acknowledgement is forthcoming from the device or devices contacted by the wearer's device within a given time, the wearer device is programmed automatically to call either a mobile telephone number or a landline telephone number, according to the wearer's prior settings.

In addition, should the symptoms progress swiftly to a high level of severity according to the stages in FIG. 1—for example the stage marked 4, at which a nebuliser should be applied—the alert may be broadcast to a medical emergency first responder service.

When the system is in elevated or high awareness mode, an increased amount of historical data 44 is referred to, and/or a higher sensor sampling rate is used, and the additional historical data and/or sensor measurements are fed into the learning model for comparative assessment, compared with the amount fed under normal operating mode. This increases computational time but also increases accuracy of model output and recognition of the patch wearer's condition. High awareness mode is sparingly used as it slows sampling time and causes the CPU to generate increased heat. Accelerated battery depletion also results. Additional data, such as the machine learning output and user feedback, are also logged in database form and stored in memory module 18.

The principal components of incoming signals as well as of predicted signals may be stored in the system as a default. Unless storage limitations dictate, the data stored also includes the raw signal. Log states from the machine learning module and wearer feedback during periods of normal breathing are not retained.

The database compiled by the processor and stored in memory module 18 is optionally, but preferably, uploaded via transceiver 26 to remote storage 60, for example cloud storage. The database may therefore be remotely accessed and used in improving the machine learning algorithm, which will be redeployed as a firmware update for the patch device components.

The model is trained on labelled clinical data. This means that process outputs are matched with the incoming data from which they are derived. This includes regular breathing signals, as well as breathing signals collected before, during and after an asthmatic event. An asthmatic event includes, but is not necessarily limited to an acute asthma attack and wheezing. For example, acoustic data may be collected using the present device placed on a subject's chest. Where the device requires hardwired download, the device may be changed every two hours (e.g. with a similarly calibrated device for consistency of data) or otherwise connected to a computer while in situ on the chest, for data to be downloaded and analysed—e.g. incorporated into the machine learning algorithm. In some embodiments, the device itself may also perform the analysis—the device therefore would only require charging but would otherwise be a substantially standalone device, un-reliant on external updating of the machine learning algorithm. Clinical data is also taken (e.g. data assembled using the AAIRS scale) and recorded periodically—e.g. every 30 minutes—during admission. Interventions such a medication administration, transfer to the ward, discharge etc will also be noted, along with any relevant questionnaires given to patients/guardians/caregivers etc. This process will allow the data and predictions made by the device to be refined and cross-checked against data acquired in a clinical setting and labelled using the current gold standard.

Although the invention has been illustrated by way of an exemplary embodiment in which EKF is employed, there are other techniques that would give similar effects. Non-limiting examples are Kalman filters and variants such as UKFs, Bayes estimators, Particle filters, time series and the like. However, it has been found by the present inventors that EKF is best suited to the medical context of the present invention.

These embodiments merely illustrate particular examples of the method, kit and apparatus of the invention providing means for the monitoring of physiological performance signals and the early prediction of the onset of an undesired medical condition. With the insight gained from this disclosure, the person skilled in the art is well placed to discern further embodiments by means of which to put the claimed invention into practice.

The invention claimed is:

1. A method of managing risk, of a subject, of suffering an adverse respiratory condition relating to a physiological system of the subject, the method using a system, the system comprising a wearable acoustic sensor, the method comprising steps of:
   a) providing the subject with the wearable acoustic sensor, operatively configured to provide an output relating to sensed cyclical events in said physiological system;
   b) providing a data processor in data communication with the wearable acoustic sensor; and
   c) causing the data processor to:
      i) monitor the output from the wearable acoustic sensor relating to said sensed cyclical events in the physiological system, wherein the data processor receives an electronic data signal representative of the output from the wearable acoustic sensor;
      ii) apply a predictive numerical model comprising Extended Kalman Filtering (EKF) to generate, from output from the wearable acoustic sensor relating to an event in a most recently observed event cycle in the physiological system, a prediction of the output from the wearable acoustic sensor in relation to a corresponding event in a future cycle in the physiological system to be observed,
      iii) compare the prediction with the output from the wearable acoustic sensor relating to the corresponding event in the future cycle in the physiological system, when observed, and
      iv) execute an output response of the system based on the comparison, the output response comprising an operation of a device that provides a stimulation.

2. The method according to claim 1, comprising performing principal component analysis on the output from the wearable acoustic sensor to identify a principal component on which to perform the EKF, and wherein EKF is performed on the identified principal component only.

3. The method according to claim 1, wherein comparing the prediction with the output from the wearable acoustic sensor comprises comparing the prediction and the output from the wearable acoustic sensor to data in a database of historical output and corresponding predictions, and determining whether the comparison with the database indicates the adverse respiratory condition is imminent, the method including allocating increased processing resources to allow for running a machine learning model when the comparison with the database yields a disparity between the prediction and the corresponding event in said future cycle in the physiological system.

4. The method according to claim 1, wherein the physiological system is the respiratory system and the adverse respiratory condition is asthma.

5. The device of claim 4, wherein the processor is configured to allocate increased processing resources to perform steps i) to iv) when the comparison yields a disparity between the prediction and the corresponding event in said future cycle in the physiological system.

6. A wearable condition-management device wearable by a subject at risk of suffering an adverse respiratory condition relating to a physiological system of the subject, the device comprising:

a) an acoustic sensor operatively configured to provide output relating to observed cyclical events in said physiological system, and b) a computer processor in data communication with the acoustic sensor, the computer processor being programmed to execute instructions causing it to:

i) monitor output from the acoustic sensor relating to said observed cyclical events in the physiological system, wherein the computer processor receives an electronic data signal representative of the output from the wearable acoustic sensor, ii) apply a predictive numerical model comprising Extended Kalman Filtering (EKF) to generate, from output from the acoustic sensor relating to an event in a most recently observed event cycle in the physiological system, a prediction of output from the acoustic sensor in relation to a corresponding event in a future cycle in the physiological system to be observed, iii) compare the prediction with the output from the acoustic sensor relating to the corresponding event in the future cycle in the physiological system when observed, and iv) execute an output response of the device based on the comparison, the output response comprising a controlled operation that provides a stimulation.

7. The device of claim 6, wherein the computer processor is programmed to perform principal component analysis on the output from the acoustic sensor to identify a principal component on which to perform the EKF, and wherein the computer processor is programmed to perform EKF on the identified principal component only.

8. The device according to claim 6, wherein the response comprises executable instructions causing the system to consult a database of historical output and predictions for determining whether the comparison indicates the adverse respiratory condition is imminent.

9. The device according to claim 6, wherein the physiological system is a respiratory system and the adverse respiratory condition is asthma.

10. The device of claim 6, wherein the sensor comprises piezo-acoustic sensing means configured for receiving frequencies characteristic of inflammation signs within an upper respiratory tract of the subject.

11. A computing system comprising the wearable condition-management device of claim 6, wherein the computing system is configured to perform the comparison by comparing the prediction and the output from the wearable acoustic sensor to data in a database of historical output and corresponding predictions, and wherein the system is configured to determine whether the comparison with the database indicates the adverse respiratory condition is imminent, and wherein the computing system is further configured to allocate increased processing resources to allow for running a machine learning model when the comparison with the database yields a disparity between the prediction and the corresponding event in said future cycle in the physiological system.

* * * * *